United States Patent
Xu et al.

(10) Patent No.: US 9,487,724 B2
(45) Date of Patent: Nov. 8, 2016

(54) LUBRICANTS FOR MAGNETIC RECORDING MEDIA

(71) Applicant: Agency for Science, Technology and Research, Singapore (SG)

(72) Inventors: Jianwei Xu, Singapore (SG); Rong Ji, Singapore (SG); Xiaobai Wang, Singapore (SG); Yan Xuan Angeline Tan, Singapore (SG); Ching Mui Cho, Singapore (SG); Chaobin He, Singapore (SG); Huiqing Xie, Singapore (SG); Wen Huei Jack Tsai, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 97 days.

(21) Appl. No.: 14/419,712

(22) PCT Filed: Aug. 7, 2013

(86) PCT No.: PCT/SG2013/000337
§ 371 (c)(1),
(2) Date: Feb. 5, 2015

(87) PCT Pub. No.: WO2014/025317
PCT Pub. Date: Feb. 13, 2014

(65) Prior Publication Data
US 2015/0184104 A1  Jul. 2, 2015

(30) Foreign Application Priority Data

Aug. 8, 2012  (SG) .................................. 201205893

(51) Int. Cl.
*C10M 105/74*  (2006.01)
*C08K 5/5399*  (2006.01)
(Continued)

(52) U.S. Cl.
CPC ........ *C10M 105/74* (2013.01); *C07F 9/65815* (2013.01); *C08K 5/5399* (2013.01);
(Continued)

(58) Field of Classification Search
CPC ............ C10M 105/74; C10M 107/48; C10M 2223/08; C10M 2223/083; C10M 2225/0405; C10N 2220/022; C10N 2220/14; C10N 2230/02; C10N 2230/08; C10N 2240/204; C10N 2270/00; C08K 5/5399; C07F 9/65815
USPC .......................................................... 508/548
See application file for complete search history.

(56) References Cited

U.S. PATENT DOCUMENTS

| | | | |
|---|---|---|---|
| 7,968,505 B2 | 6/2011 | Liu et al. | |
| 2008/0075854 A1* | 3/2008 | Stirniman | C10M 111/02 427/248.1 |

(Continued)

FOREIGN PATENT DOCUMENTS

| | | |
|---|---|---|
| WO | 2008008041 A1 | 1/2008 |
| WO | 2009141284 A1 | 11/2009 |
| WO | 2011042374 A1 | 4/2011 |

OTHER PUBLICATIONS

Written Opinion of the International Searching Authority for International Application No. PCT/SG2013/000337 dated Sep. 27, 2013, pp. 1-4.
International Preliminary Report on Patentability for International Application No. PCT/SG2013/000337 dated Feb. 19, 2015, pp. 1-6.

*Primary Examiner* — James Goloboy
(74) *Attorney, Agent, or Firm* — Winstead, P.C.

(57) ABSTRACT

The invention relates to lubricants for magnetic recording media, and in particular, to such lubricants containing cyclotriphosphazene. Methods for preparing the lubricants are also disclosed.

10 Claims, 7 Drawing Sheets

(51) Int. Cl.
*C07F 9/6581* (2006.01)
*C07F 9/6593* (2006.01)
*C10M 107/48* (2006.01)

(52) U.S. Cl.
CPC ........ *C10M107/48* (2013.01); *C10M 2223/08* (2013.01); *C10M 2223/083* (2013.01); *C10M 2225/0405* (2013.01); *C10N 2220/022* (2013.01); *C10N 2220/14* (2013.01); *C10N 2230/02* (2013.01); *C10N 2230/08* (2013.01); *C10N 2240/204* (2013.01); *C10N 2270/00* (2013.01)

(56) References Cited

U.S. PATENT DOCUMENTS

| | | |
|---|---|---|
| 2009/0023017 A1 | 1/2009 | Tomiyasu et al. |
| 2009/0110959 A1 | 4/2009 | Watanabe et al. |
| 2009/0209442 A1 | 8/2009 | Di Meo et al. |
| 2009/0297887 A1 | 12/2009 | Liu et al. |
| 2010/0246064 A1 | 9/2010 | Itoh et al. |
| 2011/0143165 A1 | 6/2011 | Kobayashi et al. |
| 2013/0330609 A1* | 12/2013 | Sawa .................... H01M 4/587 429/200 |

* cited by examiner

LUBRICANTS FOR MAGNETIC RECORDING MEDIA

CROSS-REFERENCE TO RELATED APPLICATION

This application claims the benefit of priority of Singapore Patent Application No. 201205893-9, filed Aug. 8, 2012, the contents of which being hereby incorporated by reference in its entirety for all purposes.

TECHNICAL FIELD

The invention relates to lubricants for magnetic recording media, and in particular, to such lubricants containing cyclotriphosphazene.

BACKGROUND

Heat assisted magnetic recording (HAMR) or thermal assisted magnetic recording (TAMR) are promising solutions for continuously increasing data storage recording density. Under the HAMR or TAMR conditions, the temperature of the recording medium surface will reach as high as or above the Curie temperature of the magnetic layer. This therefore requires thermally stable lubricant which can survive at 350° C., or even higher. Meanwhile, not only reliable tribological performance in hard disk drive is very critical, but also the highly thermally stable lubricant with comparable tribological properties to the commercial lubricants is an essential and critical requirement for HAMR application.

Currently, there are limited commercial lubricants which have decomposed temperatures above 300° C., such as X1-p (Dow Company) and A20H (Moresco (Matsumura Oil Research Corporation)). However, these lubricants are not quite appropriate for HAMR application mainly due to relatively low thermal stability and poor laser resistance.

SUMMARY

Present inventors have surprisingly found that by first substituting a cyclotriphosphazene moiety with six pentafluorophenoxy groups, followed by substituting the para fluorine atom of at least one of the six pentafluorophenoxy group with a perfluoropolyether (PFPE) group, the resultant lubricants show significant improvement in thermal stability as evidenced by isothermal testing at 300° C. and 350° C. Experimental results further show that about 82% of the present lubricant remained after 8 h of heating at 300° C. while all other tested conventional lubricants had about 40% or less left remaining. Most importantly, present lubricant can still withstand decomposition when exposed to heating at 350° C. for 65 min while all other tested conventional lubricants rapidly decompose with more than 90% weight loss within a very short period of time. Additionally, the laser testing demonstrated better thermal resistance than commercial lubricants under the laser irradiation, which is a necessary prerequisite for HAMR technology. In other words, present lubricants show much more reliable tribological performance in comparison with the existing commercial lubricants, further highlighting the potential application for HAMR (TAMR) systems.

Thus, in a first aspect of the disclosure, there is provided a compound of formula (I)

wherein
n is 1 to 6;
$R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3.

In a second aspect of the disclosure, a method for forming the compound of formula (I) is provided. The method may include:
reacting hexakis(pentafluorophenoxy)cyclotriphosphazene with a perfluoropolyether in a mixture of an organic solvent and a perfluorinated solvent in the presence of cesium carbonate at a temperature range of about 50 to 250° C.,
wherein the perfluoropolyether is a hydroxyl-terminated perfluoropolyether selected from the group consisting of $HOCH_2-R_f-CF_3$,
wherein $R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3.

In a third aspect of the disclosure, use of the compound of formula (I) as a lubricant is disclosed.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural changes may be made without departing from the scope of the invention. The various embodiments are not necessarily mutually exclusive, as some embodiments can be combined with one or more other embodiments to form new embodiments.

Among a variety of approaches to achieve high temperature enduring hard disk lubricants for heat assisted magnetic recording (HAMR) applications, chemically bonding perfluoropolyether (PFPE) to a cyclotriphosphazene moiety is one of the most effective methods. In addition, this type of lubricant is able to form thin and homogenous films on hard disks, providing good mobility, good bonding ratio, low surface energy, and improved thermal stability and laser resistance.

Thus, in a first aspect of the disclosure, there is provided a compound of formula (I)

wherein
n is 1 to 6;
$R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3.

As can be seen from formula (I), the compounds in formula (I) are PFPE covalently-linked cyclotriphosphazenes. Specifically, the compound is a cyclotriphosphazene which is substituted by pentafluorophenxoy groups ($C_6F_5O$) and p-PFPE-tetrafluorophenoxy groups ($OC_6F_4$-p-$OCH_2$—$R_f$—$CF_3$).

The $R_f$ used in this disclosure includes two types of hydroxy-terminated PFPEs. In exemplary embodiments, present compounds IDL1 have six substituted aromatic groups, and at least one PFPE chain attached to the para position of the tetrafluorophenoxy groups.

The term "perfluorinated" means an organic compound including all hydrogens replaced by fluorine on a carbon chain but the compound also contains at least one different atom or functional group.

In formula (I), $R_f$ can be $CF_2CF_2O(CF_2CF_2CF_2O)_mCF_2CF_2$ and m is 2 to 30, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30. Thus, $HOCH_2R_fCF_3$ has a molecular weight from about 600 to about 5,500.

In various embodiments, $R_f$ is $CF_2CF_2O(CF_2CF_2CF_2O)_mCF_2CF_2$ where m is 21.

Alternatively, in formula (I), $R_f$ can be $CF_2(OCF_2CF_2)_rO(CF_2)_s$ and r is 2 to 30, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30, and s is 0, 1, 2, or 3. Thus $HOCH_2R_fCF_3$ has a molecular weight from about 400 to about 3,000.

In various embodiments, $R_f$ is $CF_2(OCF_2CF_2)_rO(CF_2)_s$ where r is 2 and s is 2 or 3, preferably 3.

In various embodiments, n is 3.

It has been found by the inventors that compounds of formula (I) can be used as lubricants, and in particular, for lubricating magnetic recording medium. For example, lubricants containing compounds of formula (I) can have a high thermal stability, high bonding ratio and good mobility compared to conventional lubricants, and may be a good candidate for HAMR media. The compounds of formula (I) may also be potential as additives in existing lubricant system in order to improve the thermal stability, laser resistance and tribological properties.

Figure 1:
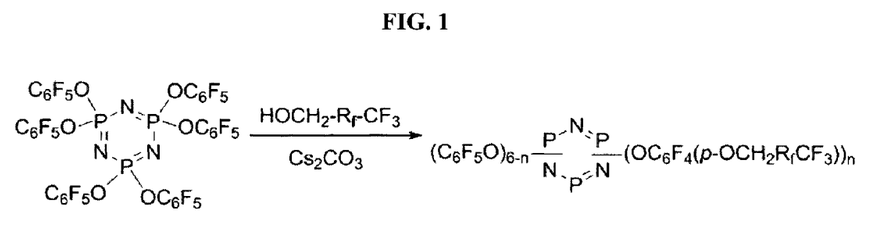
FIG. 1 shows a scheme of a chemical reaction process of forming exemplary embodiments of compounds of formula (I).

FIG. 1 shows a scheme of a chemical reaction process of forming exemplary embodiments of compounds of formula (I). The method for forming the compound of formula (I) may include:

reacting hexakis(pentafluorophenoxy)cyclotriphosphazene with a perfluoropolyether in a mixture of an organic solvent and a perfluorinated solvent in the presence of cesium carbonate at a temperature range of about 50 to 250° C.,
wherein the perfluoropolyether is a hydroxyl-terminated perfluoropolyether selected from the group consisting of $HOCH_2$—$R_f$—$CF_3$,
wherein $R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3.

In various embodiments, the hydroxyl-terminated perfluoropolyether is $HOCH_2CF_2(OCF_2CF_2)_3OCF_2CF_2CF_3$ or $HOCH_2CF_2(OCF_2CF_2)_3O(CF_2)_3CF_3$.

In various embodiments, the organic solvent is selected from the group consisting of tetrahydrofuran (THF), benzene, and methylbenzene. In certain embodiments, the organic solvent is THF.

In various embodiments, the precursor, hexakis(pentafluorophenoxy)cyclotriphosphazene, may be prepared by mixing hexachlorocyclotriphosphazene and a pentafluorophenoxide in a tetrahydrofuran solvent.

In further embodiments, the pentafluorophenoxide may be prepared by a reaction between a pentafluorophenol and a base solution including $K_2CO_3$, $Na_2CO_3$, KOH, NaOH or NaH in an organic solvent such as THF.

In one embodiment, a desired amount of hexachlorocyclotriphosphazene and sodium pentafluorophenoxide was placed into a reaction vessel to afford hexakis(pentafluorophenoxy)cyclotriphosphazene. The second step involved substitution of para-fluorine atom in the pentafluorophenoxy groups by one or several hydroxy-terminated PFPE chains in the presence of anhydrous cesium carbonate in a mixture of THF solvent and fluorinated solvent such as FC77. The THF may be replaced by another suitable solvent such as benzene, methylbenzene, or the like. The fluorinated solvent may be a perfluorinated solvent selected from FC77™, HFE 7100™, PF5060™, and the like. Some of these solvents are commercially available from Dupont™ or 3M™ Novec™. A suitable solvent in the Vertrel™ family of solvents may also be used. The pure product may be obtained by simple separation processes including washing and centrifuging to remove the impurity.

In summary, present compounds and lubricants exhibit better thermal stability when compared with the currently available products. Present compounds and lubricants also show better laser resistance than the commercial lubricants under the same experimental conditions. This may address the thermal stability issue of the lubricant in HAMR and TAMR.

Furthermore, present compounds can be used as lubricants or additives in combination with commercial products to achieve even better performance such as higher thermal stability and better mobility.

In order that the invention may be readily understood and put into practical effect, particular embodiments will now be described by way of the following non-limiting examples.

EXAMPLES

Example 1

Preparation of Lubricant IDL1

The precursor hexakis(pentafluorophenoxy)cyclotriphosphazene may be prepared by the following method: To a dry tetrahyfuran (THF) solution of pentafluorophenol (0.05 mol), sodium hydride (0.06 mol) was added. The reaction was stirred at 60° C. for 2 h. Hexachlorocyclotriphosphazene was added in one potion. The mixture was stirred for 12 h. Crude product was separated by silica gel column chromatography to give rise to a pure precursor. The chemical structure of the precursor was confirmed by $^{1}$H nuclear magnetic resonance (NMR) and $^{31}$P NMR.

To a solution of hexakis(pentafluorophenoxy)cyclotriphosphazene, hydroxy-terminated PFPE (0.3 equivalent) was added. The reaction was stirred at a temperature of 50-250° C. for 5-48 h in the presence of anhydrous $CsCO_3$. $^{1}$H NMR and $^{31}$P NMR were used to confirm the chemical structure of the final product.

Example 2

Viscosity Measurement

Similar to traditional lubricants, the viscosity of lubricant IDL1 has shown to behave like a Newtonian liquid. The dynamic viscosity of lubricants together with several commercially available lubricants for comparison at 25° C. is given in Table 1.

TABLE 1

Viscosity Data for IDL1 vs. Commercial Lubricants

| Lubricants | Viscosity at 25° C. (mPa · s) | Viscosity at 40° C. (mPa · s) | Viscosity at 100° C. (mPa · s) |
| --- | --- | --- | --- |
| IDL1 | 625 | 337 | 79 |
| X1-p | 729 | 259 | 9 |
| A20H | 65[a] | —[a] | —[a] |
| Z-Tetraol | 500[a] | —[a] | —[a] |

[a]Not measured.

Example 3

Surface Free Energy of Thin Film and Carbon-Lubricant Bonding Ratio

Lubricant IDL1 forms uniform thin films on disk surfaces with a thickness of 0.8-2.4 nm. Table 2 and Table 3 show the surface energies and bonding ratios of lubricant films measured with the same thickness of IDL1 and commercial lubricants. It is observed that present lubricant shows comparable surface energy and, in some cases, higher bonding ratio than those of the commercial lubricants.

TABLE 2

Surface Energy Comparison of IDL1 and Commercial Products

| Lubricants | Surface Energy @ 25° C. |
| --- | --- |
| Z-DOL(2K) | 44 |
| A20H | 44 |
| Z-Tetraol | 25 |
| IDL1 | 41 |

TABLE 3

Bonding Ratio of Lubricant IDL1 and Commercial Products

| Lubricants | Bonding Ratio @ 25° C. |
| --- | --- |
| Z-DOL(2K) | 2 |
| A20H | 20 |
| Z-Tetraol | 9 |
| IDL1 | 13 |

Example 4

Mobility Measurement of Lubricant Thin Films

Figure 2:
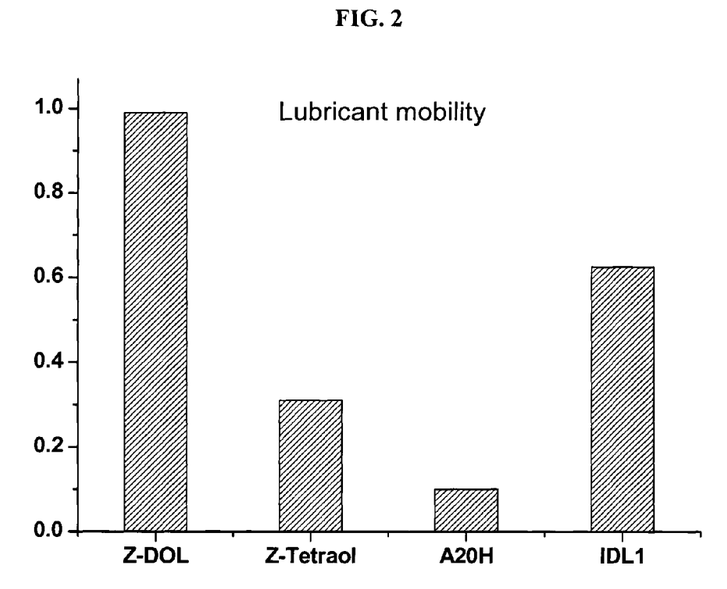
FIG. 2 is a bar graph showing lubricant film recovery for different lubricants measured with TOF-SIMS (Z-DOL is used for reference).

The mobility of the lubricants was tested using time-of-flight secondary ion mass spectroscopy (TOF-SIMS). In these tests, a film of each respective lubricant was formed uniformly on a disk surface. A local area in the film (a radial "stripe" approximately 40 μm wide) was depleted of the lubricant. The rate at which each lubricant film re-flew back into the depleted area on the disk surface was measured using TOF-SIMS. The recovery by the respective lubricant in the depleted area after 1 h was examined; the recovery rate was used to indicate the lubricant film mobility. As shown in FIG. 2, the mobility of A20H film was found to be much lower than that of Zdol 2000 film: the latter showed complete recovery while the former showed little recovery. In comparison, lubricant IDL1 showed a moderate mobility. As can be appreciated, excess mobility may lead to lubricant spin-off and lubricant film dewetting, decreasing the durability of the hard disk, while poor mobility may result in loss of lubrication in some areas on the disk surface. Thus, moderate mobility may be desirable for a lubricant used in magnetic recording applications.

Example 5

Fiction Coefficients Measurement of Lubricant

Figure 3:
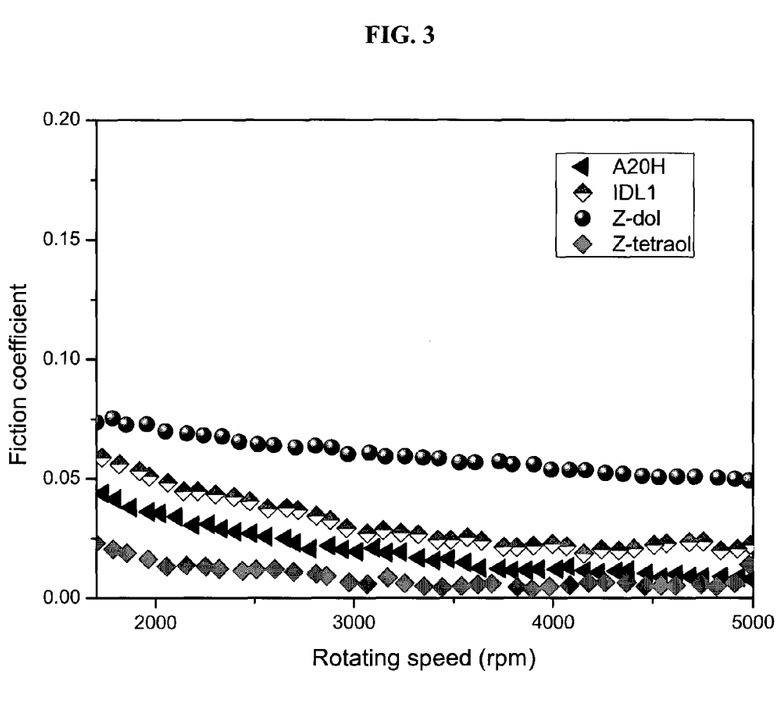
FIG. 3 shows the friction coefficient of IDL1 and selected commercial lubricants.

The dynamic friction coefficients of thin films of IDL1 along with Z-DOL, A20H and Z-Tetraol lubricants were measured. The films were deposited on the surfaces of magnetic hard disks and their friction coefficients were measured using CETR reliability tester (skew angle was 0°, vertical load was 2.5 g). As illustrated in FIG. 3, the results showed that lubricant IDL1 had comparable dynamic friction coefficients to those of the conventional lubricants, indicating that lubricant IDL1 has comparable tribological behavior to the existing commercial lubricants.

Example 6

Characterization of Laser Adsorption

Figure 4A:
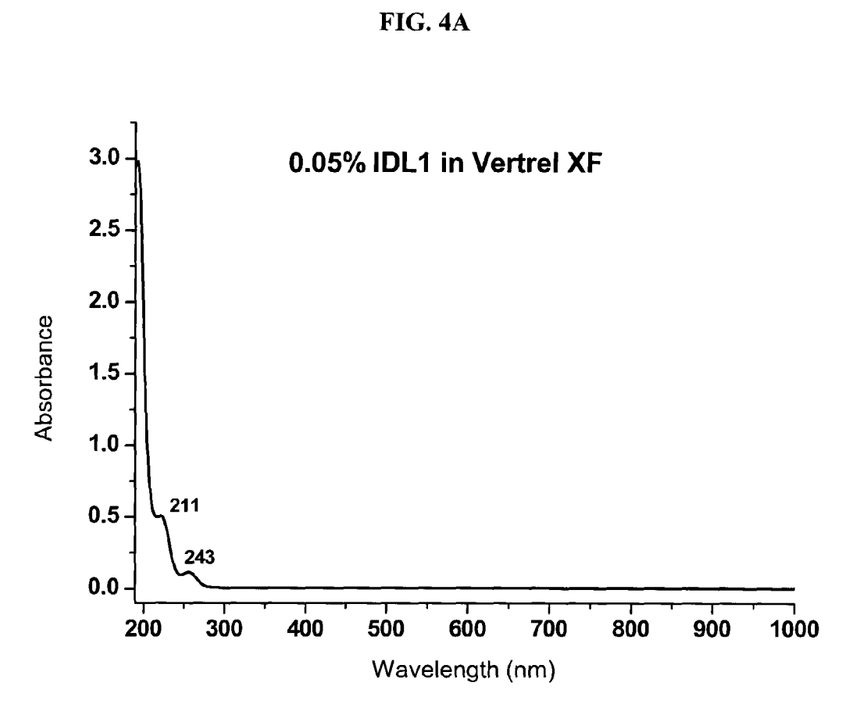
FIG. 4A shows the laser adsorption of IDL1 solution.
Figure 4B:
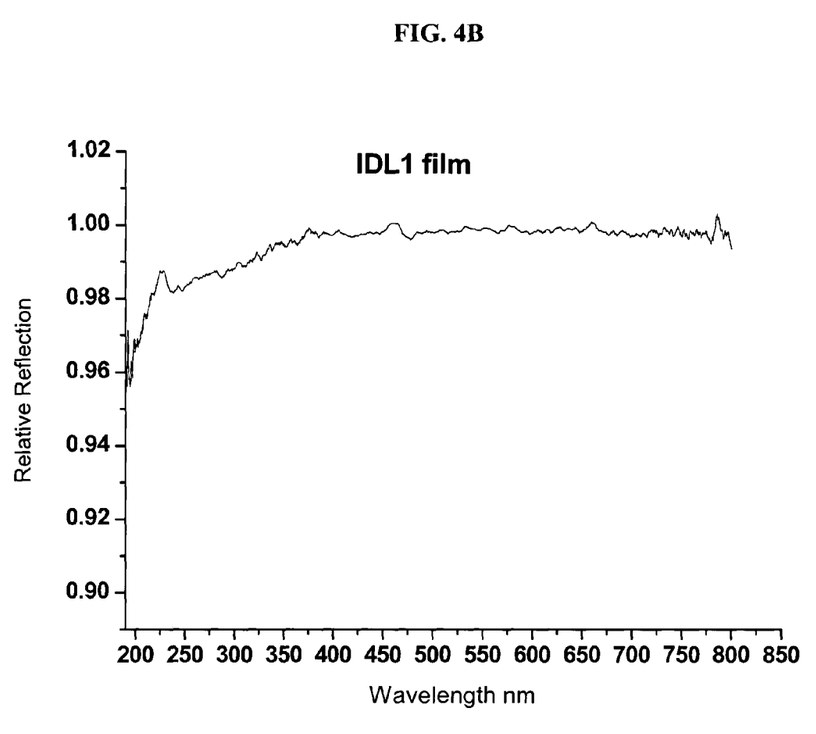
FIG. 4B shows the laser reflection of IDL1 thin film.

Laser adsorption measurement was performed using the lubricant solution and the lubricant film on hard disk surface. As shown in FIG. 4, IDL1 shows the similar laser performance to commercial lubricants, which no noticeable adsorption was observed in the laser wavelength range of 380 to 800 nm for both IDL1 solution and IDL1 film. The photo-effect is completely negligible, however, thermal effect is expected be dominated particularly for red light laser source which is now being used by many researchers for HAMR application.

Example 7

Characterization of Lubricant Thermal Stability

TGA experiments were conducted to study the relative thermal stability in the air. The temperatures at which weight loss of 5% and 20% occurs are given in Table 4.

TABLE 4

Decomposition Temperatures of Lubricants

| lubricants | Temp. at weight loss @ 5% (° C.) | Temp. at weight loss @ 20% (° C.) |
|---|---|---|
| IDL1 | 305 | 421 |
| Z-DOL(2K) | 183 | —[a] |
| Z-DOL(4K) | 200 | —[a] |
| X1-P | 304 | 336 |
| A20H(3K) | 319[b] | —[a] |
| Z-tetraol | 230[b] | —[a] |

[a]no data
[b]Reference data

The effect of the heating rate on the decomposition temperature of lubricant was studied and the data are summarized in Table 5. As the lubricant is heated up to a very high temperature within a very short period, for instance, 1 second, by using a laser source in HAMR, this experiment is likely to provide evaluation on whether the lubricant on the surface of a disk can survive at very high heating rate. In an experiment, if the heating rate is increased to be 200° C./min, the recorded decomposition temperature of IDL1 can reach up to 350° C.

TABLE 5

Heat Rate vs. Decomposition Temperature of IDL1

| Heating rate (° C./min) | Temp. at weight loss @ 5% (° C.) | Temp. at weight loss @ 20% (° C.) |
|---|---|---|
| 20 | 304.6 | 420.9 |
| 50 | 310.7 | 425.2 |
| 100 | 332.2 | 453.1 |
| 150 | 342.5 | 466.4 |
| 200 | 350.3 | 476.0 |

Figure 5A:
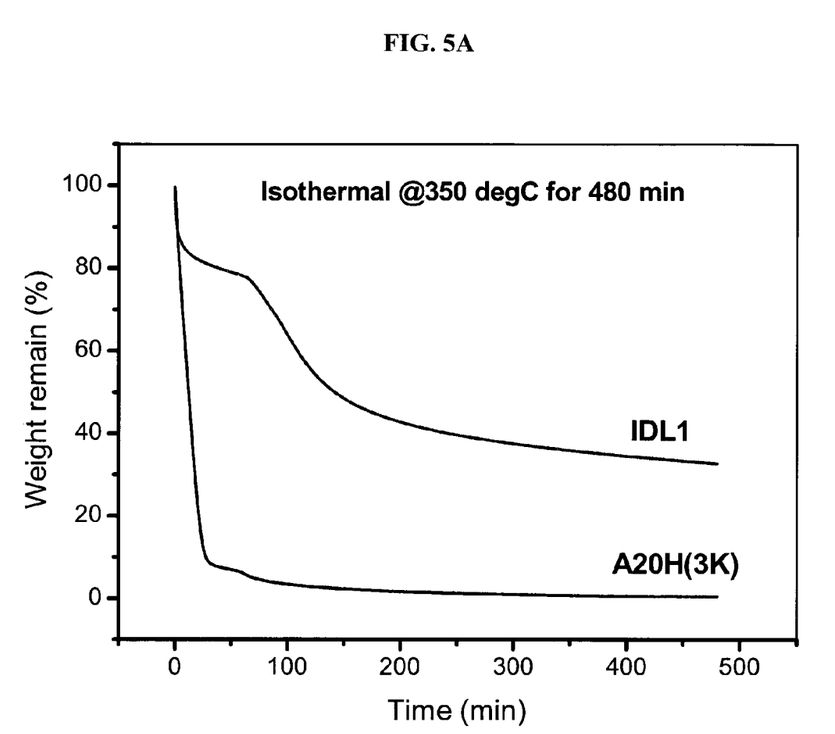
FIG. 5A and FIG. 5B show the thermal aging effect on the thermal stability of various lubricants measured by TGA at 350° C. and 300° C., respectively.
Figure 5B:
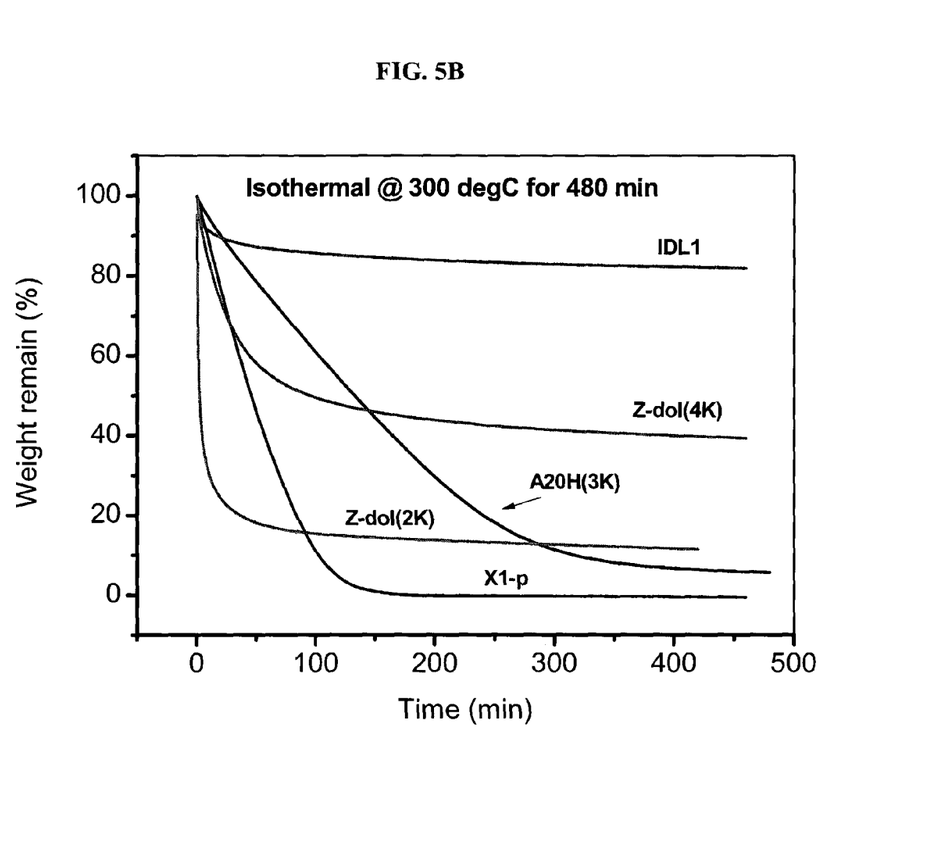

The thermal aging tests were also conducted at 250° C., 300° C. and 350° C. for about 8 h. The weight loss under such conditions may indicate the long term thermal stability of the lubricant (FIG. 5). Table 6 gives the comparison data of IDL1 and commercial products. The results indicated that under 300° C., IDL1 still has more than 80% left. However, less than 40% was retained for all the commercial lubricants. Even if IDL1 was heated at 350° C., it still can survive for 65 min with less than around 20% weight loss. In contrast, A20H quickly lost more than 90% weight within 30 min.

TABLE 6

Comparison of Thermal Stability of IDL1 and Commercial Products at 250, 300, and 350° C. for 480 min

| | Weight % after 480 min @ | | |
|---|---|---|---|
| Lubricants | 250° C. | 300° C. | 350° C. |
| IDL1 | 89 | 82 | 32 |
| Z-DOL(2K) | 25 | 11 | — |
| Z-DOL(4K) | 68 | 39 | —a |
| X1-P | 48 | 0 | —a |
| A20H(3K) | 92 | 6 | 0 |

Example 8

Thermal Effect Induced by Laser on the Thermal Stability of Lubricant Film

Figure 6:
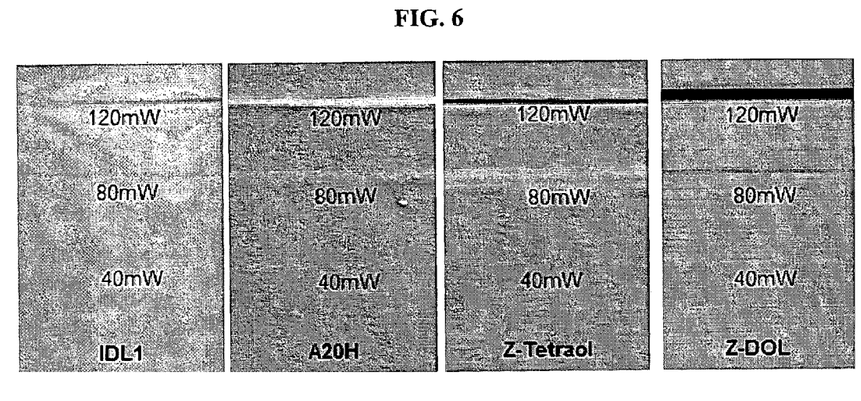
FIG. 6 shows the laser irradiation on different lubricated disks. Laser irradiation: 200 ns and cooling down period: 30 ms, 400 pulses of laser shined on every spot along a straight line.
Figure 7A:
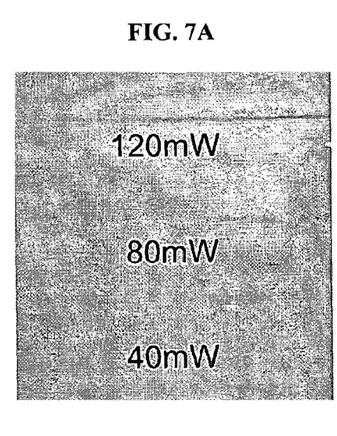
FIG. 7A and FIG. 7B show the laser irradiation with difference duration on IDL1 lubricated disks: (A) 200 ns on and 30 ms off laser, and 20 pulses of 5 ns on; and (B) 5 ns off laser shine on the same spot 400 times on IDL1 lubricated disk, respectively.
Figure 7B:
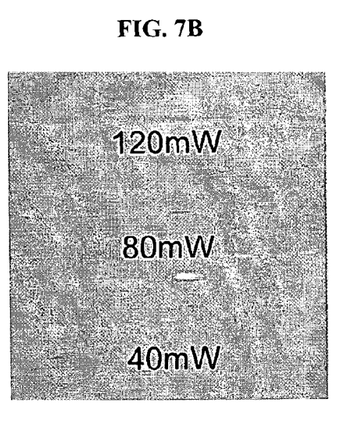

A laser light with a wavelength of 785 nm was focused onto 1 μm size beam and irradiated on different lubricated disks. FIG. 6 shows the film optical surface analysis images after laser irradiation at power of 120 mW, 80 mW and 40 mW. Z-DOL lubricant film started to be affected with 40 mW power as a faint line was observed. It was completely damaged under laser with a power of 120 mW. However, other lubricant films are intact under 40 mW laser irradiation. At 120 mW and 80 mW power, the damage order is Z-DOL>Z-Tetraol>A20H>>IDL1. TOF-SIMS analysis showed that IDL1 decreased only slightly in lubricant thickness, while the other lubricant films showed significant lubricant degradation and decomposition. On the above experiment, the laser pulse width and size are purposely set much bigger than the laser beam on hard disk drive for practical HAMR application, since laser irradiation duration in hard disk drive is in fact at a nanosecond level. Using more practical laser irradiation conditions, the laser experiments of lubricant film of IDL1 were carried out and optical surface analysis images are shown in FIG. 7. IDL1 lubricant films are intact under the 40 mW and 80 mW laser irradiation for 5 ns.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A compound of formula (I)

(I)

wherein
n is 1 to 6;
$R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3.

2. The compound of claim 1, wherein n is 3.

3. The compound of claim 1 or 2, wherein $R_f$ is $CF_2CF_2O(CF_2CF_2CF_2O)_mCF_2CF_2$, and wherein m is 21.

4. The compound of claim 1 or 2, wherein $R_f$ is $CF_2(OCF_2CF_2)_rO(CF_2)_s$, and wherein r is 2 and s is 3.

5. A compound of formula (IDL1)

(IDL1)

6. A method for forming the compound of formula (I)

(I)

wherein
n is 1 to 6;
$R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3, the method comprising:
reacting hexakis(pentafluorophenoxy)cyclotriphosphazene with a perfluoropolyether in a mixture of an organic solvent and a perfluorinated solvent in the presence of cesium carbonate at a temperature range of about 50 to 250° C.,
wherein the perfluoropolyether is a hydroxyl-terminated perfluoropolyether comprising $HOCH_2$—$R_f$—$CF_3$,
wherein $R_f$ is defined above.

7. The method of claim 6, wherein the hydroxyl-terminated perfluoropolyether is $HOCH_2CF_2(OCF_2CF_2)_3OCF_2CF_2CF_3$ or $HOCH_2CF_2(OCF_2CF_2)_3O(CF_2)_3CF_3$.

8. The method of claim 7, wherein the organic solvent is selected from the group consisting of tetrahydrofuran, benzene, and methylbenzene.

9. The method of claim 6, wherein the hexakis(pentafluorophenoxy)cyclotriphosphazene is prepared by mixing hexachlorocyclotriphosphazene and a pentafluorophenoxide in a tetrahydrofuran solvent.

10. A method for lubricating a magnetic recording medium, comprising applying a lubricant comprising a compound of formula (I) to the magnetic recording medium, (I)

wherein
n is 1 to 6;

$R_f$ is selected from the group consisting of $CF_2CF_2O(CF_2CF_2CF_2O)_mCF_2CF_2$ wherein m is 2 to 30 and $CF_2(OCF_2CF_2)_rO(CF_2)_s$ wherein r is 2 to 30 and s is 0, 1, 2, or 3.

* * * * *